United States Patent [19]

Edwards

[11] Patent Number: 5,643,200

[45] Date of Patent: Jul. 1, 1997

[54] DEVICE AND METHOD FOR BACKFLUSHING AN IRRIGATION-ASPIRATION HANDPIECE TIP

[76] Inventor: James J. Edwards, 2139 W. Royalton Rd., Broadview Heights, Ohio 44147

[21] Appl. No.: 404,595

[22] Filed: Mar. 15, 1995

[51] Int. Cl.⁶ .................................................. A61M 1/00
[52] U.S. Cl. ................ 604/27; 604/36; 604/294; 604/905
[58] Field of Search ............... 604/27, 240–243, 604/905, 294, 35, 36, 39, 43, 173, 272, 34

[56] References Cited

U.S. PATENT DOCUMENTS

| | | | |
|---|---|---|---|
| 4,508,532 | 4/1985 | Drews et al. | |
| 4,519,385 | 5/1985 | Atkinson et al. | 604/27 X |
| 4,650,461 | 3/1987 | Woods | |
| 4,652,255 | 3/1987 | Martinez | 604/27 |
| 4,714,460 | 12/1987 | Calderon | 604/28 |
| 4,734,091 | 3/1988 | Boyle et al. | 604/54 |
| 4,891,044 | 1/1990 | Mitchell | 604/27 |
| 4,904,238 | 2/1990 | Williams | 604/43 |
| 4,941,872 | 7/1990 | Felix et al. | 604/27 |
| 4,955,887 | 9/1990 | Zirm | |
| 4,982,739 | 1/1991 | Hemstreet et al. | 128/750 |
| 5,038,755 | 8/1991 | Kepley | |
| 5,162,043 | 11/1992 | Gahn | |
| 5,294,325 | 3/1994 | Liu | 204/418 |
| 5,470,312 | 11/1995 | Zanger et al. | 604/34 |

*Primary Examiner*—Michael Powell Buiz
*Assistant Examiner*—V. Alexander
*Attorney, Agent, or Firm*—Renner, Otto, Boisselle & Sklar, P.L.L.

[57] ABSTRACT

A system for backflushing an irrigation-aspiration handpiece tip includes a source of backflushing fluid, a syringe for injecting the fluid through an aspiration tube of an irrigation-aspiration handpiece, the aspiration tube of the handpiece being connected to an aspiration tube of the irrigation-aspiration handpiece tip, and a coupling device for connecting the syringe to the aspiration tube of the irrigation-aspiration handpiece. The coupling device includes an inlet end and an outlet end, a receptacle at the inlet end for receiving the syringe and a passageway extending between the receptacle and the outlet end for passage of the backflushing fluid. The outlet end of the coupling device connects to the aspiration tube to complete the connection between the syringe and the aspiration tube of the irrigation-aspiration handpiece.

15 Claims, 1 Drawing Sheet

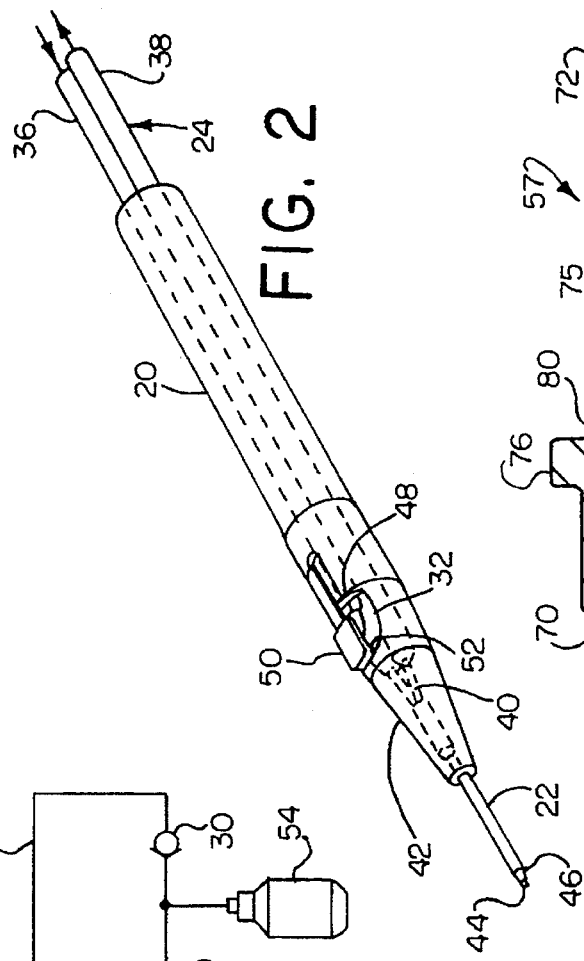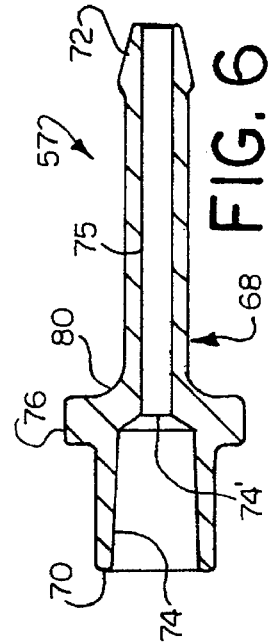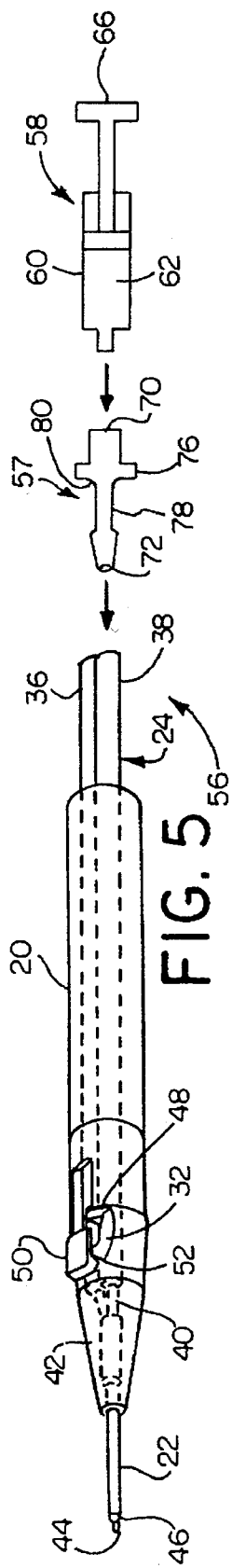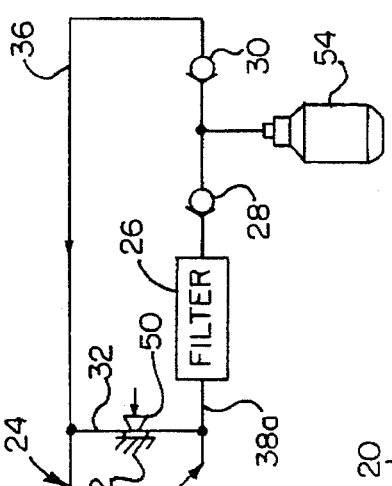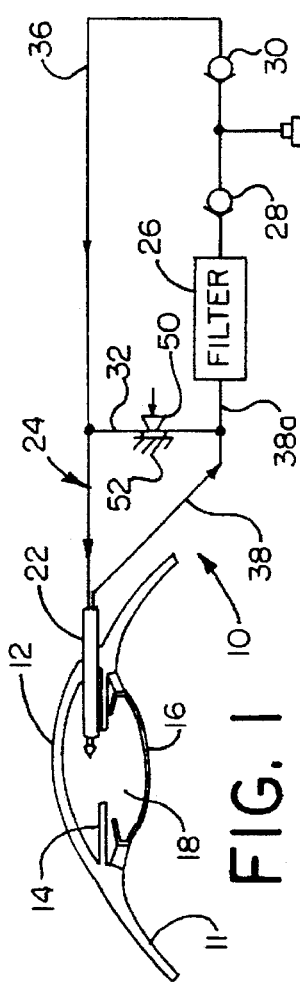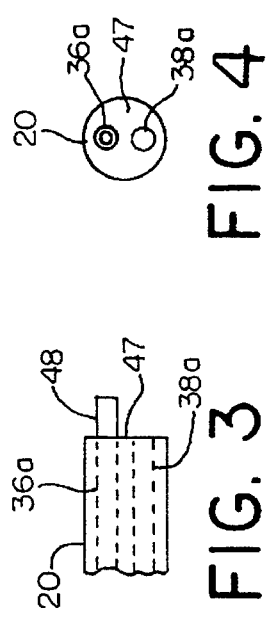

5,643,200

DEVICE AND METHOD FOR BACKFLUSHING AN IRRIGATION-ASPIRATION HANDPIECE TIP

TECHNICAL FIELD OF THE INVENTION

The present invention relates to a device and method for backflushing an irrigation-aspiration handpiece, and especially the tip thereof or used therewith, used during extracapsular cataract surgery, such as during irrigation and aspiration steps.

BACKGROUND OF THE INVENTION

A growing problem in modern society is the ever-rising cost of medical care. Contributing to the rising costs of medical care is the price for medical equipment, and more particularly, for surgical tools. Surgical tools are expensive to purchase and may become useless after one or only several uses, for example, due to the affects of use, sterilization, or for other reasons. Accordingly, devices which extend the useful life of a surgical tool are a welcome addition to the medical field since such devices reduce the need repeatedly to purchase new surgical equipment.

The present invention extends the useful life of a tool used in extracapsular cataract surgery. In the surgical art of extracapsular cataract surgery, the lens contents are pulverized while a saline solution is irrigated into and aspirated from the eye. One exemplary procedure to remove the nucleus of the lens is referred to as expressing the lens. Another exemplary procedure to fragment the nucleus is known as phacoemulsification. In phacoemulsification the nucleus is fragmented and most of the fragments, preferably all, are removed. After completion of removal of the nucleus an irrigation-aspiration handpiece is used to remove any remaining nuclear material and, primarily, cortical lens material. The fragmented cataract which is composed of nuclear and cortical material is withdrawn along with the irrigation liquid by or during the aspiration mode of the surgical procedure.

An exemplary device which irrigates and aspirates the lens capsule, for example, after the phacoemulsification procedure, includes an irrigation-aspiration tip having approximately a 0.1 to 0.3 mm aspiration opening and an aspiration passageway for removal of the fragmented nuclear and cortical material. Due to the small size of such opening and/or passageway, and the unique quality of the lens material, e.g. sticky, gooey, glue-like, etc., even like a solid plasma, some of the aspirated nuclear and cortical material may become stuck and not pass completely through the tip. If this occurs, when the tip is sterilized the nuclear or cortical material still remaining in the tip "bakes" onto the inner surface of the tip's passageway, thereby obstructing the passageway. This may render the device useless for subsequent extracapsular surgeries until the irrigation-aspiration tip is replaced.

The device used for irrigation and aspiration also includes a handpiece to an end of which the irrigation-aspiration tip usually is connected. This device can cost as much as $2500, with the individual tips costing approximately $500 each. Accordingly, every time a tip becomes obstructed by the "baked" nuclear or cortical material, the tip must be replaced, which, as is indicated, is at substantial cost. Currently, ophthalmic surgeons are forced to replace a number, for example, as many as five or even more, of tips per year due to obstruction from "baked" nuclear or cortical material.

The present invention relates to a device and method to backflush the irrigation-aspiration device, and particularly the irrigation-aspiration tip, thereby removing nuclear and cortical material remaining in the tip after completion of cataract surgery. Therefore, when the tip is sterilized, there will be no nuclear or cortical material remaining that can "bake" onto the inner surface of the tip's passageway and obstruct the passageway. Thus, the present invention provides an efficient, economical device and method for extending the useful life of irrigation-aspiration devices, and particularly aspiration tips.

SUMMARY OF THE INVENTION

Briefly according to one embodiment of the invention a system for backflushing the tip of an irrigation-aspiration handpiece includes a source of backflushing fluid, a means for injecting the fluid through an aspiration tube of the irrigation-aspiration handpiece tip, and a means for connecting the injection means and aspiration tube together.

In another embodiment of the invention, the injection means is connected to an aspiration tube of an irrigation-aspiration handpiece which is connected to the aspiration tube of the irrigation-aspiration handpiece tip. The injection means and aspiration tube of the irrigation-aspiration handpiece are connected by a coupling device which includes a body with an inlet end and an outlet end. The coupling device also includes a receptacle at the inlet end for receiving the injection means, and a passageway extending between the receptacle and the outlet end for passage of the backflushing fluid. The outlet end of the coupling device is connected to the aspiration tube. In a preferred embodiment, the outlet end is tapered and inserted into the aspiration tube such that a substantially fluid-tight seal is created.

In another embodiment of the invention, a syringe is used to inject the backflushing fluid into the aspiration tube and the receptacle is a tapered bore which receives an end of the syringe.

In still another embodiment of the invention, the body of the coupling device is made out of surgical steel.

In another embodiment of the invention, the liquid which is injected through the aspiration tube is a saline solution.

In another embodiment of the invention, a method for backflushing the tip of an irrigation-aspiration handpiece includes connecting the inlet end of a coupling device to a source of backflushing fluid and connecting the outlet end of the coupling device to an aspiration tube of an irrigation-aspiration handpiece, connecting the aspiration tube of the irrigation-aspiration handpiece to the aspiration tube of the irrigation-aspiration handpiece tip if not already connected thereto, and forcing backflushing fluid through the coupling device, the aspiration tube of the irrigation aspiration handpiece, and the aspiration tube of the tip.

The foregoing and other features of the invention are hereinafter fully described and particularly pointed out in the claims, the following description and the annexed drawings setting forth in detail a certain illustrative embodiment of the invention, this being indicative, however, of but one of the various ways in which the principles of the invention may be employed.

BRIEF DESCRIPTION OF THE DRAWINGS

FIG. 1 is a schematic view of an exemplary irrigation-aspiration system used in extracapsular cataract surgery.

FIG. 2 is a perspective view of an exemplary irrigation-aspiration handpiece.

FIG. 3 is a fragmentary side view of another irrigation-aspiration handpiece.

FIG. 4 is a back view of the handpiece of FIG. 3.

FIG. 5 is schematic view of a backflushing system in accordance with the principles of the present invention.

FIG. 6 is a sectional view of a coupling device for connecting a source of fluid to an irrigation-aspiration handpiece for backflushing in accordance with the principles of the present invention.

DETAILED DESCRIPTION

Referring first to FIGS. 1 and 2 of the drawings, an irrigation-aspiration system 10 used in extracapsular cataract surgery is shown with a human eye 11. The eye 11 includes, in part, the cornea 12, the iris 14, and the posterior capsule 16. The entire chamber 18 of the eye 11 following such type of surgery is normally filled with aqueous humor.

The irrigation-aspiration system 10 illustrated in FIG. 1 includes a tubular handpiece 20 with a fine needle-like tip 22 at one end. A flexible tube system 24 with appropriate filters, valves, pumps, etc. provides a fluid flow path to supply fluid, such as a saline solution, to irrigate the eye 11 and to aspirate fluid from the eye 11. The flexible tube system 24 is connected to respective irrigation and aspiration passages (sometimes also referred to as tubes) which extend through the handpiece 20 and communicate with the needle-like tip 22, as is best shown in FIG. 2. A liquid pump (not shown) may be operated to pump fluid through the tube system 24, handpiece 20 and tip 22 to irrigate the eye 11. The liquid pump could be a mechanical or electrical pump, a flexible syringe, a bottle, pack or other supply of fluid located above the patient to rely on gravity flow pumping, or some other type of pumping device. The same or a separate pump, vacuum source, etc., may be used to provide the desired suction for the aspiration tubes, passages, etc. An example of such an irrigation-aspiration system is disclosed in U.S. Pat. No. 4,650,461, the entire disclosure of which hereby is incorporated by reference.

The tube system 24 has an irrigation tube 36 and an aspiration tube 38 which may be separate or integrally and continuously connected along their length. Portions of tubes 36 and 38 are connected to respective passages 36a, 38a, of the handpiece 20 in side-by-side relationship and communicate with corresponding passages or tubes in the needle-like tip 22 via connectors 40. The terminal end of the tip 22 has an axial inlet 44 in fluid communication with the aspiration tube 38a and a pair of diametrically opposed outlets 46 in fluid communication with the irrigation tube 36a. Small irrigation and aspiration passages or tubes (not shown) in the tip 22 connect the inlet 44 and outlets 46 with the respective tubes 36a, 38a. The tubes 36a, 38a may be flexible or rigid tubes in the handpiece 20, as is depicted in FIGS. 2 and 5, for example. The tubes 36a, 38a alternatively may be passageways in the body of the handpiece 20, as is depicted in FIGS. 3 and 4, for example. In the embodiment of FIGS. 3 and 4 the passageway 36a is terminated at the back end 47 of the handpiece 20 by a connector extension 48 and the passageway 38a terminates at a flush opening in the back end 47. The invention may be used with other types of handpieces, tubes and passageways.

After the irrigation-aspiration procedure has been completed, and the nuclear and cortical material removed from the eye 11, the handpiece 20 and needle-like tip 22 can be backflushed to remove any nuclear and cortical particles which may still be within the aspiration tube 38a, or aspiration tube of the tip 22 of the irrigation-aspiration handpiece 20.

FIG. 5 is a schematic illustration of an exemplary backflush system according to the invention for backflushing the tip 22 after use, for example, in the above-summarized surgery. As is illustrated, the backflush system 56 includes a coupling device 57 and a source 58 of pumpable backflushing fluid. The source 58 may be a syringe 60 containing liquid 62 which is used to flush out any nuclear or cortical material which remains within the aspiration tube 38a or the aspiration tube of the tip 22. The coupling device 57 enables the syringe 60 to be coupled to the aspiration tube 38a of the irrigation-aspiration handpiece 20. The coupling device 57 attaches at one end to the syringe 60, and at the other end to the aspiration tube 38a of the irrigation-aspiration handpiece 20. After the syringe 60 is coupled to the aspiration tube 38a via the coupling device 57, manual pressure can be applied to the plunger 66 of the syringe 60 to inject the liquid 62 through the coupling device 57 and into the aspiration tube 38a. The liquid 62 passes through the aspiration tube 38a, the aspiration tube of the tip 22, and the inlet 44 flushing any cortical matter from the aspiration tube 38a or the aspiration tube of the tip 22.

The coupling device 57 is best illustrated in FIG. 6. The coupling device 57 includes a body 68 having an inlet end 70 and an outlet end 72. The body 68 also includes a receptacle 74 at the inlet end 70 for connecting to the syringe 60. A passageway 75 through the body 68 extends between one end 74' of the receptacle 74 and the outlet end 72 of the coupling device 57.

The body 68 of the coupling device 57 is constructed of surgical steel. For example, T-31-6 high-grade surgical steel is used in the preferred embodiment of the coupling device 57. The coupling device 57 could also be made out of materials other than surgical steel; preferably such materials would permit the device to be sterilizable and, therefore, reusable.

The receptacle 74 in the preferred embodiment of coupling device 57 is designed to receive an end of a standard syringe. Accordingly, the receptacle 74 is a tapered bore which is approximately 0.29 inches long. The bore tapers at a rate of ¾ of an inch per foot, or, in other words, on a 3°, 34', 48" included angle. The use of a tapered bore as a receptacle is only exemplary of a structure for attaching the coupling device 57 to the syringe 60. If a different apparatus were used for injecting fluid through the coupling device 57, the handpiece 20, and the tip 22, such as a pump, a syringe with a threaded outlet fitting, or some other device, the coupling device 57 could be attached using any of a number of different methods. For example, the receptacle 74 could be threaded so that the outlet of the liquid pump or syringe could be screwed into the receptacle of the coupling device 57. Preferably the connection between the syringe 60 and the coupling device 57 is relatively fluid tight so there is relatively little fluid leakage at the connection during use.

Approximately ¼ inch from the inlet end 70 is an integral grip 76. The grip 76 is radially enlarged and knurled to permit manual or instrument grasping of the coupling device 57 with relative ease, for example, to assemble the coupling device 57 in the backflush system 56. The grip 76 of the preferred embodiment is approximately 0.38 inches in diameter and has an axial length of approximately 0.10 inches.

Extending from the grip 76 to a shaft 78 of the coupling device 57 is a radius of curvature 80 of approximately 0.08 inches. The radius of curvature 80 gives greater overall strength to the coupling device 57 than would be present if the grip 76 and shaft 78 of the coupling device 57 were to meet at a right angle. However, the radius of curvature 80 and its relative dimensions are merely exemplary of methods for reinforcing the connection area between the grip 76 and the shaft 78 of the coupling device 57. Other methods of reinforcing that connection could be employed as one skilled in the art would readily recognize.

The shaft 78 extends away from the radius of curvature 80 towards the outlet end 72 of the coupling device 57. The outlet end 72 of the coupling device 57 is insertable into the aspiration tube 38a of the irrigation-aspiration handpiece 20. In order to provide a substantially liquid-tight seal between the coupling device 57 and the aspiration tube 38a, the outlet end 72 tapers gradually. In the preferred embodiment of the present invention, this taper may be approximately 20 degrees, thus making it relatively easy to create a seal between the aspiration tube 38a and the outlet end 72. It will be recognized by those skilled in the art, that the tapered outlet end 72 is but one way of connecting the coupling device 57 to the aspiration tube 38a. For example, the outlet end 72 could be straight. In such a case, the outlet end 72 may be inserted into a flexible aspiration tube 38a, and the aspiration tube 38a may be clamped around the outside surface of the outlet end 72. Moreover, the degree of tapering of the outlet end 72 is exemplary and a greater or lesser degree of tapering may be used to perform the liquid sealing function.

The syringe 60 which serves to store the source of liquid 62 for the backflushing procedure and also serves to inject the liquid through the coupling device 57 into the aspiration tube 38a and out the inlet end 44, is but an exemplary apparatus for transferring the liquid from a source through the coupling device 57 and into the aspiration tube 38a. For example, a roller pump or other mechanical or electrical devices could be substituted for the syringe 60 without departing from the scope of the present invention.

As previously mentioned, backflushing of the irrigation-aspiration handpiece tip 22, extends the useful life thereof. The coupling device 57 enables the backflushing liquid to be coupled to the aspiration tube 38a of the handpiece 20 to flush the aspiration tube 38a of the handpiece 20 and aspiration tube of the tip 22 with liquid under pressure. As was also mentioned above, tips may be ruined due to buildup of nuclear or cortical material which becomes stuck and then "baked" in the aspiration tube of the tip 22 upon sterilization. At a cost of 9500 per tip, it can be readily seen that the present invention can substantially reduce the costs associated with the purchase of surgical equipment when performing cataract surgery.

Although the invention has been shown and described with respect to an exemplary embodiment thereof, it will be evident that equivalent alterations and modifications will occur to others skilled in the art upon the reading and understanding of the specification. The present invention includes all such equivalent alterations and modifications, and is limited only by the scope of the following claims.

I claim:

1. A system for backflushing an irrigation-aspiration handpiece tip and aspiration tube connected therewith for cleaning after use for aspiration, said system comprising:
   a source of backflushing fluid;
   a means for injecting said fluid through said aspiration tube of said irrigation-aspiration handpiece tip while disconnected from an irrigation-aspiration source; and
   a means for connecting said means for injecting to said aspiration tube of said irrigation-aspiration handpiece tip to couple said backflushing fluid thereto to backflush said irrigation-aspiration handpiece tip.

2. A system according to claim 1, wherein said means for connecting comprises:
   an irrigation-aspiration handpiece having an aspiration tube;
   a body having an inlet end and an outlet end;
   a receptacle at said inlet end for receiving said injecting means; and
   a passageway extending between said receptacle and said outlet end for passage of said backflushing fluid, wherein said outlet end is connected to said aspiration tube of said irrigation-aspiration handpiece, and said aspiration tube of said irrigation-aspiration handpiece is connected to said aspiration tube of said irrigation aspiration handpiece tip.

3. A system according to claim 2, wherein said outlet end is tapered for insertion into said aspiration tube of said irrigation-aspiration handpiece.

4. A system according to claim 3, wherein said taper of said outlet end creates a fluid-tight seal between said outlet end and said aspiration tube of said irrigation-aspiration handpiece.

5. A system according to claim 2, wherein said injecting means is a syringe.

6. A system according to claim 5, wherein said receptacle is a tapered bore for receiving said syringe.

7. A system according to claim 2, wherein said body is comprised of surgical steel.

8. A system according to claim 1, wherein said backflushing fluid is a saline solution.

9. A coupling device for connecting a source of backflushing fluid to an irrigation-aspiration handpiece having a tip and an aspiration tube for backflushing the tip coupled to the handpiece while disconnected from an irrigation-aspiration source, said coupling device comprising:
   a body having an inlet end and an outlet end;
   a receptacle at said inlet end for connecting said body to said source of backflushing fluid;
   a passageway extending from said receptacle to said outlet end for passage of said backflushing fluid; and
   means for connecting said outlet end to said aspiration tube of said irrigation-aspiration handpiece to direct backflushing fluid through the tip to clean the tip while disconnected from an irrigation-aspiration source.

10. A coupling device according to claim 9, wherein said receptacle is a tapered bore which receives a syringe.

11. A coupling device according to claim 9, wherein said means for connecting comprises a tapered outlet end which is inserted into said aspiration tube of said irrigation-aspiration handpiece.

12. A coupling device according to claim 11, wherein the taper of said outlet end creates a fluid-tight seal between said outlet end and said aspiration tube of said irrigation-aspiration handpiece.

13. A coupling device according to claim 9, wherein said body is made of surgical steel.

14. A method of cleaning an irrigation-aspiration handpiece having a tip and an aspiration tube, said method comprising the steps of:
   subsequent to use of said tip and said aspiration tuba for aspiration, disconnecting the aspiration tube of said irrigation-aspiration handpiece from a source of aspiration;
   connecting an inlet end of a coupling device to a source of backflushing fluid;
   connecting an outlet end of said coupling device to the aspiration tube of the irrigation-aspiration handpiece; and
   forcing said backflushing fluid through said coupling device to backflush said aspiration tube of said irrigation-aspiration handpiece and said tip of said irrigation-aspiration handpiece.

15. A method according to claim 14, wherein said backflushing fluid is injected to remove nuclear and cortical material.

* * * * *